United States Patent
Crisco et al.

(10) Patent No.: US 9,125,784 B2
(45) Date of Patent: Sep. 8, 2015

(54) ARM POSITIONING CUSHION

(71) Applicant: Merit Medical Systems, Inc., South Jordan, UT (US)

(72) Inventors: Larry Van Thomas Crisco, Atlanta, GA (US); James Bradley Hess, Roswell, GA (US); Gary G. Goff, Canton, GA (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 13/940,541

(22) Filed: Jul. 12, 2013

(65) Prior Publication Data

US 2014/0059772 A1    Mar. 6, 2014

Related U.S. Application Data

(60) Provisional application No. 61/693,919, filed on Aug. 28, 2012.

(51) Int. Cl.
*A61G 13/12* (2006.01)
*A61G 7/075* (2006.01)
(Continued)

(52) U.S. Cl.
CPC .......... *A61G 13/1235* (2013.01); *A61F 5/3761* (2013.01); *A61G 13/124* (2013.01); *A61F 5/0118* (2013.01); *A61G 7/075* (2013.01); *A61G 13/1295* (2013.01); *A61G 2005/125* (2013.01)

(58) Field of Classification Search
CPC . A61G 7/075; A61G 13/1235; A61G 13/124; A61G 13/1295; A61G 2005/125; A61F 5/0118; A61F 5/3761
See application file for complete search history.

(56) References Cited

U.S. PATENT DOCUMENTS

| 3,242,923 A | 3/1966 | Jacoby, Sr. |
| 3,747,916 A | 7/1973 | Benson |

(Continued)

FOREIGN PATENT DOCUMENTS

| GB | 2472246 | 2/2007 |
| WO | WO2005090072 | 9/2005 |

OTHER PUBLICATIONS

Brasselet et al., 'comparison of Operator Radiation Exposure with Optimized Radiation Protection Devices During Coronary Angiograms and Ad Hoc Percutaneous Coromary Interventions by Radial and Femoral Routes', European Heart Journal, 2008, 29:63-70.

(Continued)

*Primary Examiner* — Robert G Santos
*Assistant Examiner* — Brittany Wilson
(74) *Attorney, Agent, or Firm* — Stoel & Rives LLP (57) ABSTRACT

An arm positioning cushion for locating and supporting an arm of a patient above a base surface and in an orientation suitable for vascular radial access procedures. The arm positioning cushion includes a forearm support having a fingers contact surface at a first height above the base surface, an upwardly-curved wrist contact surface having an centerline apex at a second height above the base surface, and a first coupling portion. The arm positioning cushion also includes an elbow support having an elbow contact surface at a third height of the base surface, and a second coupling portion configured for linear-adjustable engagement with the first coupling portion to adjustably couple the forearm support to the elbow support. The third height is greater than the first height and less than the second height. In one aspect, the forearm support and elbow support may comprise a substantially homogeneous cushion material throughout.

20 Claims, 10 Drawing Sheets

(51) Int. Cl.
*A61F 5/37* (2006.01)
*A61G 5/12* (2006.01)
*A61F 5/01* (2006.01)

(56) References Cited

U.S. PATENT DOCUMENTS

| | | |
|---|---|---|
| D249,360 S | 9/1978 | Lacock |
| D266,345 S | 9/1982 | Bigham et al. |
| D267,028 S | 11/1982 | Spisak |
| 4,369,774 A | 1/1983 | Robbins |
| 4,576,351 A | 3/1986 | Brink |
| 4,662,366 A | 5/1987 | Tari |
| 4,665,574 A | 5/1987 | Filips et al. |
| 4,674,110 A | 6/1987 | Eaton et al. |
| D299,539 S | 1/1989 | Kennedy |
| D318,923 S | 8/1991 | Marsh |
| D333,520 S | 2/1993 | Mann |
| 5,263,497 A | 11/1993 | Grabenkort et al. |
| 5,291,903 A | 3/1994 | Reeves |
| 5,339,834 A | 8/1994 | Marcelli |
| 5,342,290 A | 8/1994 | Schuellein |
| 5,372,145 A | 12/1994 | Berger |
| D362,072 S | 9/1995 | Sternberg |
| 5,549,121 A | 8/1996 | Vinci |
| 5,601,597 A | 2/1997 | Arrowood et al. |
| 5,623,951 A | 4/1997 | Kamaya |
| 5,785,057 A | 7/1998 | Fischer |
| D402,036 S | 12/1998 | Parsley et al. |
| 5,845,643 A | 12/1998 | Vergano et al. |
| D407,820 S | 4/1999 | Sullenberger et al. |
| D412,191 S | 7/1999 | Woo |
| 5,940,912 A | 8/1999 | Keselman et al. |
| D413,982 S | 9/1999 | Swedberg et al. |
| D415,281 S | 10/1999 | Swedberg et al. |
| 5,981,964 A | 11/1999 | McAuley et al. |
| D422,362 S | 4/2000 | Ames |
| D424,698 S | 5/2000 | Ames |
| D426,307 S | 6/2000 | Swedberg et al. |
| 6,101,650 A | 8/2000 | Omdal et al. |
| 6,153,666 A | 11/2000 | Lagace |
| 6,267,115 B1 | 7/2001 | Marshel |
| 6,357,066 B1 | 3/2002 | Pierce |
| 6,378,149 B1 | 4/2002 | Sanders et al. |
| 6,467,487 B1 | 10/2002 | Rios |
| 6,497,673 B2 | 12/2002 | Rogalski |
| 6,568,010 B1 | 5/2003 | Ames |
| 6,647,986 B1 | 11/2003 | Korotko et al. |
| 6,663,055 B2 | 12/2003 | Boucher et al. |
| D487,512 S | 3/2004 | Bradshaw et al. |
| 6,725,481 B1 | 4/2004 | Marshall |
| 6,898,810 B2 | 5/2005 | Steven |
| D518,894 S | 4/2006 | Kirn |
| 7,020,917 B1 | 4/2006 | Kolody et al. |
| 7,057,194 B2 | 6/2006 | Goldstein |
| 7,274,031 B2 | 9/2007 | Smith |
| D555,250 S | 11/2007 | Wells |
| 7,406,967 B2 | 8/2008 | Callaway |
| 7,520,007 B2 | 4/2009 | Skripps |
| D618,354 S | 6/2010 | Francucci et al. |
| 7,978,825 B2 | 7/2011 | Ngo |
| D649,253 S | 11/2011 | Held |
| D652,935 S | 1/2012 | Held |
| D657,468 S | 4/2012 | Held |
| 8,369,933 B2 | 2/2013 | Crisco et al. |
| 2002/0080921 A1 | 6/2002 | Smith et al. |
| 2004/0143177 A1 | 7/2004 | Falbo, Sr. et al. |
| 2004/0216233 A1 | 11/2004 | Ludwig et al. |
| 2005/0043805 A1 | 2/2005 | Chudik |
| 2005/0091749 A1 | 5/2005 | Humbles |
| 2006/0016006 A1 | 1/2006 | Whitmore et al. |
| 2006/0200061 A1 | 9/2006 | Warkentine |
| 2007/0011814 A1 | 1/2007 | Rotert |
| 2007/0152197 A1 | 7/2007 | Lagrace et al. |
| 2007/0286340 A1 | 12/2007 | Cadwalader et al. |
| 2008/0245373 A1 | 10/2008 | Kounkel |
| 2009/0000625 A1* | 1/2009 | Alfery .......................... 128/878 |
| 2009/0172884 A1 | 7/2009 | Semlitsch |
| 2009/0250073 A1* | 10/2009 | Alfery et al. ................. 128/878 |
| 2010/0305431 A1 | 12/2010 | Cristo et al. |
| 2011/0184278 A1 | 7/2011 | Goff et al. |
| 2012/0170710 A1 | 7/2012 | Niedzielski et al. |
| 2012/0241652 A1 | 9/2012 | Jeschke |

OTHER PUBLICATIONS

Pristipino et al., 'Major Improvement of Percutaneous Cardiovascular Procedure Outcomes with Radial Artery Catheterization: Results from the PREVAIL Study', Heart (British Cardiac Society), 2009, 95:476-82.

International Search Report and Written Opinion dated May 11, 2010 for PCT/US2010/034452.

* cited by examiner

FIG. 13

ARM POSITIONING CUSHION

CROSS-REFERENCE TO RELATED APPLICATIONS

This application claims the benefit of U.S. Provisional Patent Application No. 61/693,919, filed Aug. 28, 2012.

BACKGROUND

The present invention relates generally to arm positioning devices for use in the medical arts, and in particular to an arm positioning cushion that locates and supports the arm of a patient in an orientation suitable for vascular radial access procedures.

Coronary diseases remain a leading cause of morbidity and mortality in Western societies and are treated using a number of approaches. It is often sufficient to treat the symptoms with pharmaceuticals and lifestyle modification to lessen the underlying causes of the disease. In more severe cases, however, it may be necessary to treat the coronary disease using interventional medical procedures such as cardiac catheterization. Cardiac catheterization procedures generally utilize a thin catheter passed through a major artery to access a patient's heart. In the United States, the femoral artery (near the inner thigh) is most frequently used during cardiac catheterization procedures. Recent medical advancements, however, suggest that use of the radial artery (near the wrist) is more convenient and may reduce both the length of the procedure and the risk of complications during the procedure. Despite these benefits, many doctors still remain reluctant to perform cardiac catheterization via the radial artery. One reason for this reluctance is the radial artery being smaller and more challenging to access than the femoral artery, with correspondingly smaller sheaths and different techniques being required for placing the catheter guide.

Existing equipment used for supporting and positioning the patient's arm during radial cardiac catheterization procedures have numerous drawbacks that make it difficult for doctors to perform cardiac catheterization via the radial artery. For example, existing arm support and alignment apparatus are often complicated and difficult to position around a patients body, and are therefore uncomfortable to both the patient and the physician. In addition, the existing apparatus may also be non-absorbent of the blood and other fluids which may be spilled during the procedure, contain components that are difficult to clean to current hospital standards, or cannot be easily adjusted to fit differently-sized patients.

SUMMARY OF THE INVENTION

The present disclosure seeks to overcome the problems presented in the prior art by providing an adjustable, absorbent and disposable arm positioning cushion that increases patient comfort while presenting and securing the hyper-extended wrist of the patient in an orientation that is more suitable for vascular radial access procedures.

The entire disclosure of U.S. Provisional Patent Application No. 61/693,919, filed Aug. 28, 2012, is incorporated herein by reference as if set forth in its entirety.

These and various other advantages, features, and aspects of the present invention will become apparent and more readily appreciated from the following detailed description of the embodiments taken in conjunction with the accompanying drawings, as follow.

Those skilled in the art will appreciate and understand that, according to common practice, various features of the drawings discussed below are not necessarily drawn to scale, and that dimensions of various features and elements of the drawings may be expanded or reduced to more clearly illustrate the embodiments of the present invention described herein.

DETAILED DESCRIPTION

The following description is provided as an enabling teaching of exemplary embodiments. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances, and are a part of the invention. Thus, the following description is provided as an illustration of the principles of the embodiments and not in limitation thereof, since the scope of the invention is to be defined by the claims.

Illustrated in FIGS. 1-9 is a representative embodiment of an arm positioning cushion for positioning and supporting the arm of a patient above a base surface and in an orientation that is highly suitable for vascular radial access procedures, including procedures for both diagnostic and intervention purposes such as the cardiac catheterization procedures discussed above. The arm positioning cushion of the present disclosure provides several significant advantages and benefits over other devices and methods for positioning and supporting a patient's arm, as described in further detail below. However, the recited advantages are not meant to be limiting in any way, as one skilled in the art will appreciate that other advantages may also be realized upon practicing the present disclosure. It is also to be appreciated that the arm positioning cushion disclosed herein may not be limited to uses relating to vascular radial access procedures, and that other uses and applications are also possible and may be considered to fall within the scope of the present disclosure.

Figure 1:
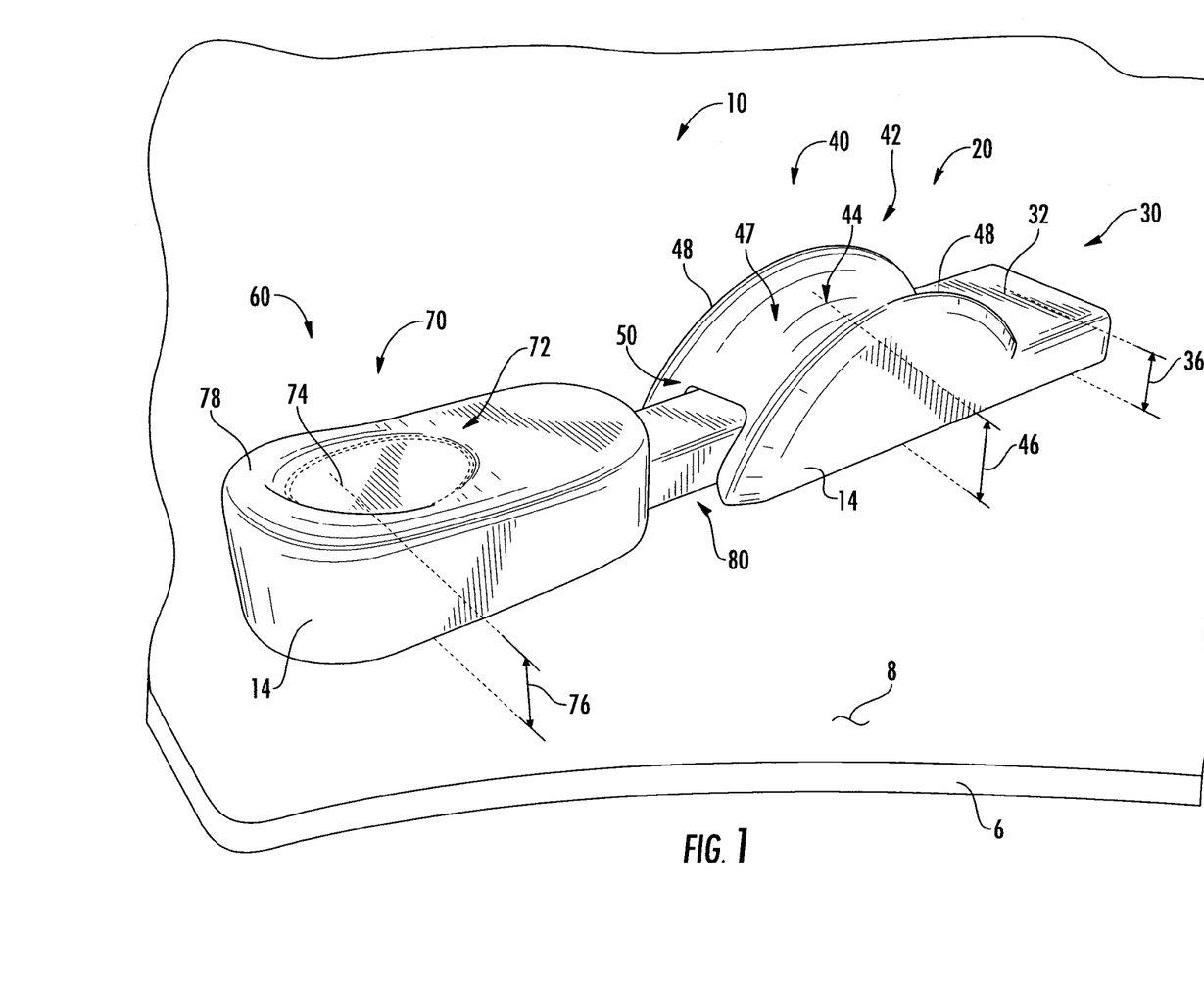
FIG. 1 is a perspective view of an arm positioning cushion, in accordance with a representative embodiment of the disclosure.
Figure 2:
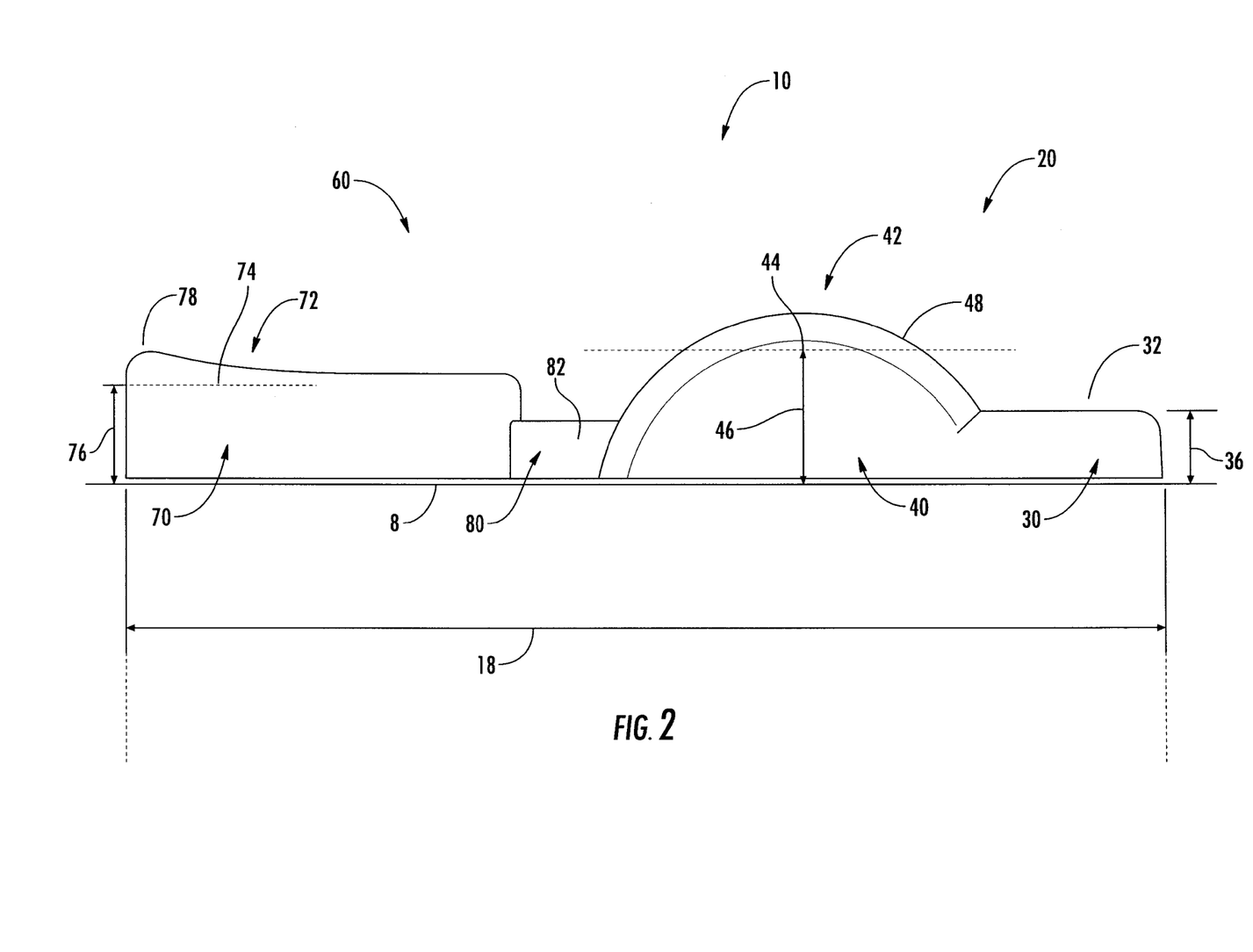
FIG. 2 is a right side view of the arm positioning cushion of FIG. 1.
Figure 3:
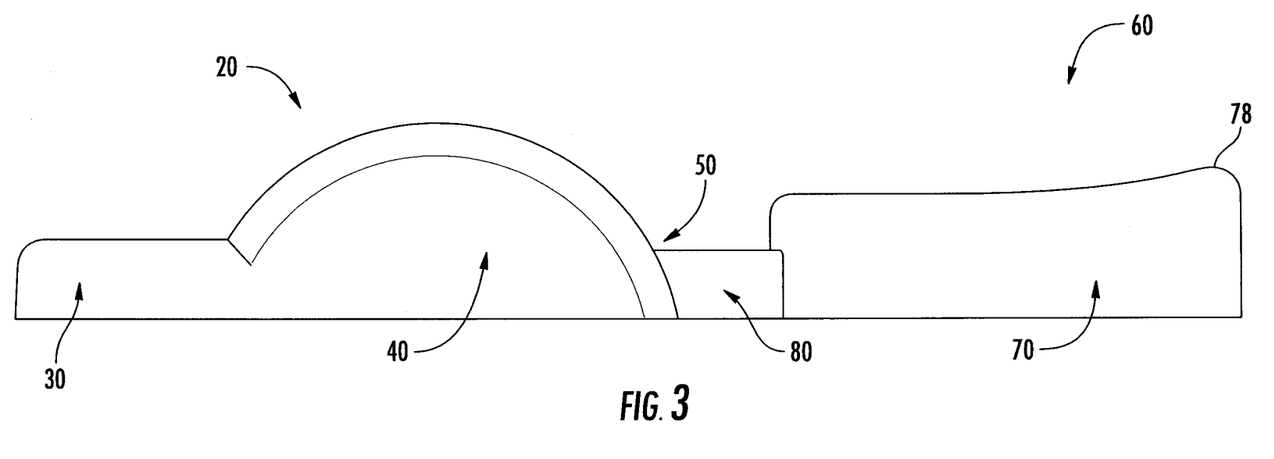
FIG. 3 is a left side view of the arm positioning cushion of FIG. 1.

As shown in FIG. 1, the arm positioning cushion 10 includes a forearm support 20 having a fingers rest portion 30 and a wrist support portion 40, and an elbow support 60 having an elbow cradle portion 70. Although not entirely visible in the drawing, the forearm support also includes a first coupling portion 50 which interrelates with a second coupling portion 80 formed into the elbow support 60. The forearm support 20 and the elbow support 60 can be two independent pieces that are manufactured separately and then assembled together to form the arm positioning cushion 10. Alternatively, the forearm support 20 and the elbow support 60 can be manufactured together and then separated using a separation or cutting process.

The forearm support 20 and the elbow support 60 can be substantially homogenous bodies that are formed from a cushioning material 14. The cushioning material 14 can be resilient or at least partially compressible. In addition, the cushioning material 14 can be an absorbent or at least a semi-absorbent material which absorbs blood and other fluids which may be released or spilled during the vascular procedure. In one aspect, the cushioning material 14 can be a polyethylene foam that includes both the cushioning and absorbency aspects described above. It is to be appreciated, moreover, that in other embodiments the forearm support 20 and the elbow support 60 can be made from other cushioning materials which may or may not be absorbent and which may or may not be substantially homogenous. For instance, it is contemplated that one or both of the forearm support 20 and the elbow support 60 can be provided with an outer or top layer having different cushioning and/or absorbent properties than an underlying base layer. In other aspects of the present disclosure, the forearm support 20 and the elbow support 60 can be made from differing materials.

The arm positioning cushion 10 of the present disclosure may also be adapted for disposal after a single use. In this case, the cushioning material 14 forming the forearm support 20 and the elbow support 60, as well as their method of manufacture, can be pre-selected for immediate disposal after use, such as in a medical waste products incinerator. Making the forearm support 20 and the elbow support 60 from substantially homogenous bodies of the same cushioning material 14 can assist with this process by limiting the number and type of volatile compounds that may be released during incineration, along with the selection of the cushioning material 14 for producing by-products that are chemically inert, non-toxic and environmentally benign.

As stated above, the arm positioning cushion 10 is configured for positioning and supporting an arm of a patient above a base surface 8 and in an orientation suitable for vascular radial access procedures. With additional reference to FIGS. 10-13, in many cases the patient 90 will be lying prone on an operating table 2 having a top surface 4, with one of his/her arms extending away from the body and resting on a side support 6 having an upper surface which serves as the base surface 8. The side support 6 may extend or project from underneath the operating table 2 to locate the base surface 8 at a height that is one to two inches below the top surface 4 of the operating table 2, so that the patient's arm extends slightly downwardly, as well as outwardly, from the patient's shoulder that is resting on the top surface 4 of the operating table 2.

With the arm positioning cushion 10 located on the base surface 8 (or as shown, on a sterile cloth overlying the base surface), the patient's elbow 94 can then be supported within the elbow cradle portion 70 of the elbow support 60 and the back of the patient's wrist 96 and hand 98 can be folded over the wrist support portion 40 of the forearm support 20. This provides two primary contact surfaces, namely the elbow contact surface 72 and the wrist contact surface 42, for positioning and securing the patient's arm 92 or forearm 95. The back of the patient's fingers 99 can then rest lightly on the fingers contact surface 32 located atop the fingers rest portion 30 of the forearm support 20. In some aspects, the fingers 99 of the patient 90 may be additionally secured to the fingers rest portion 30 with a strap or medical tape 38 to further secure the patient's arm in position.

Referring back to FIGS. 1-8, both the wrist contact surface 42 and the elbow contact surface 72 can include surface features which function to position and secure the patient's arm. In particular, the wrist contact surface 42 can comprise the rounded upper or top surface of the semi-circular wrist support portion 40 that is configured to position the wrist of the patient in a hyperextended position, exposing the radial artery for ease of vascular access. The wrist support portion 40 can further include side ridges 48 that project upwardly on both sides of the wrist support portion 40 to form the wrist contact surface 42 into a rounded groove 47 structure that operates to limit the rotation, or pronation/supination, of the patient's wrist. Thus, as shown in the drawings, the wrist contact surface 42 can be curvilinear in two dimensions to both position and stabilize/immobilize the wrist.

The wrist support portion 40 can further include a centerline apex 44 located in the center of the groove 47 and at the top of the wrist support portion 40. The height 46 of the centerline apex 44 above the base surface 8 (FIGS. 1-2) can serve to define the height of the patent's wrist as the back of the wrist and hand of the patient are folded over the top of the wrist support portion 40. The side ridges 48 can resiliently press against the sides of the patients' wrist to center the wrist within the groove 47, especially with embodiments where the entire forearm support 20 is made from a resilient, cushioning material 14.

The elbow contact surface 72 of the elbow cradle portion 70 can also include surface features that function to position and secure the elbow and forearm of the patient. In the exemplary embodiment shown in FIGS. 1-8, for instance, the elbow contact surface 72 includes a depression 74 and a U-shaped back ridge 78 that can resiliently press against the sides of the patient's elbow to center the elbow within the depression 74. As can be seen, the height 76 of the depression 74 above the base surface 8 can serve to define the height of the patent's elbow once the elbow is settled within the elbow cradle portion 70 of the elbow support 60.

The fingers rest portion 30 includes a fingers contact surface 32 that is located at a height 36 above the base surface 8, and which can provide a resilient surface against which the tops of the fingers may comfortably rest during the vascular procedure.

The shape and height of the rounded, semi-circular wrist support portion 40 is configured to position and support the wrist 96 of the patient 90 in a mild-to-moderate hyperextended position (FIGS. 12-13), which orientation presents the radial artery 47 in a manner suitable for vascular radial access procedures. At the same time, the hyperextended position can help to reduce or alleviate the stress on the patient's wrist 96 and forearm 95 which can result when the wrist of the patient is placed in a strongly hyperextended position, as may be found in certain hand support devices available in the prior art.

Figure 4:
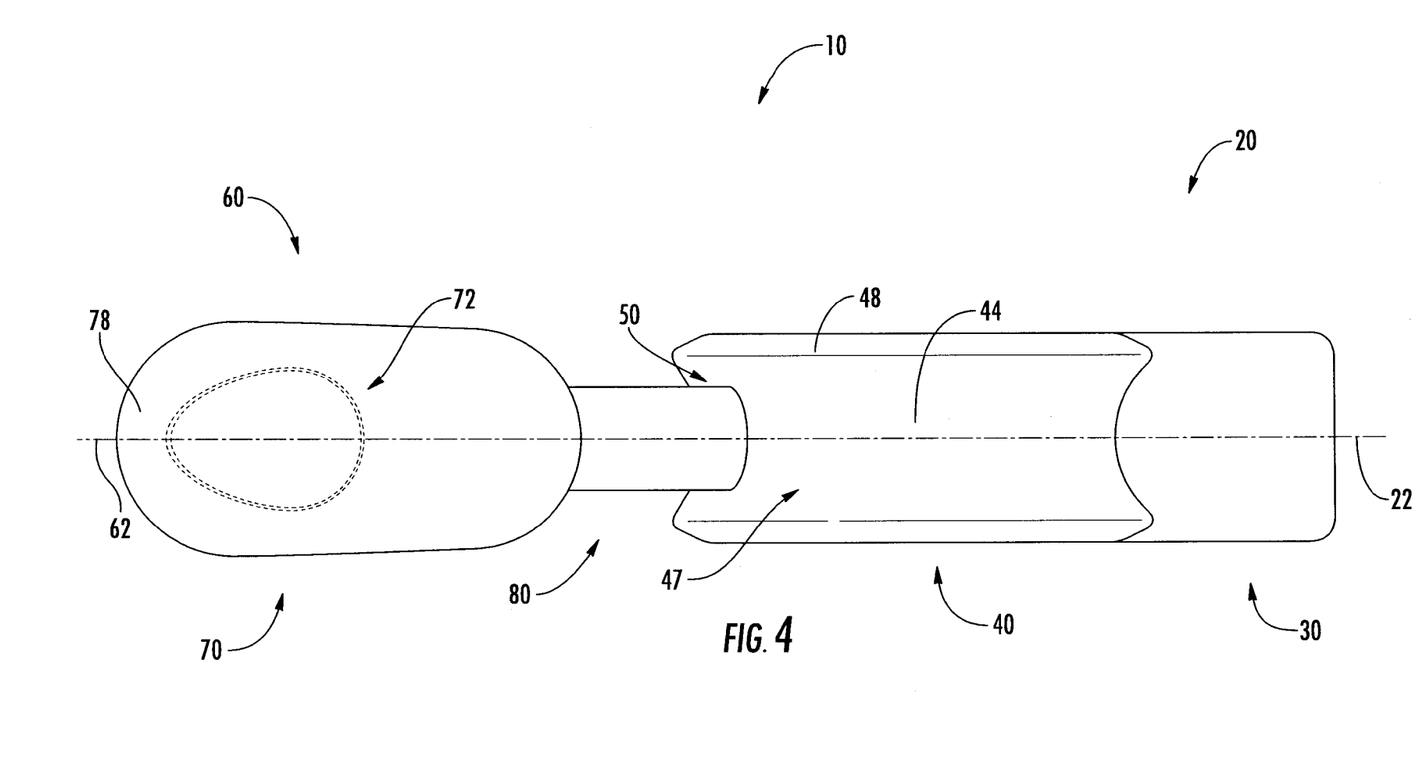
FIG. 4 is a top view of the arm positioning cushion of FIG. 1.
Figure 5:
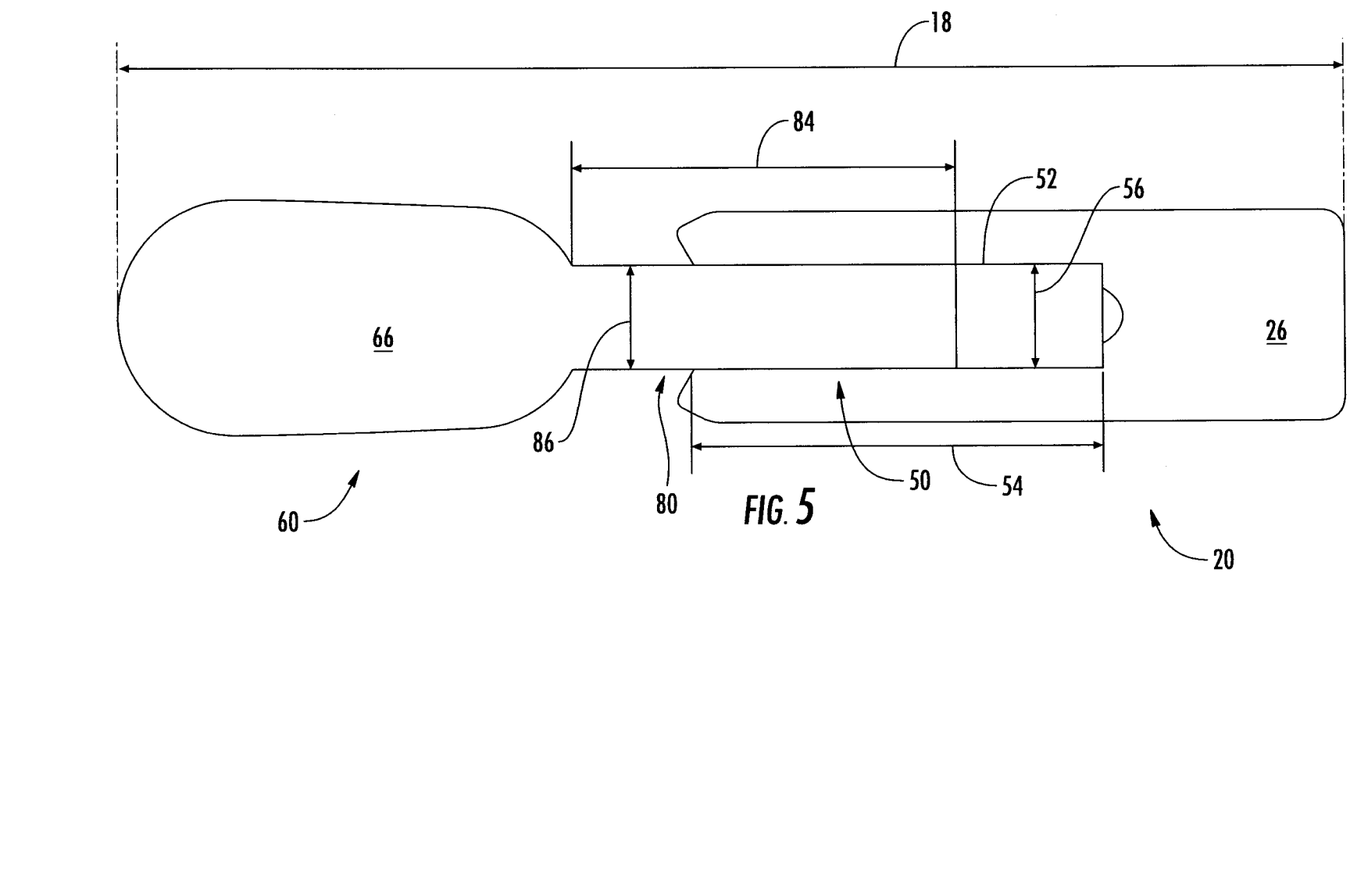
FIG. 5 is a bottom view of the arm positioning cushion of FIG. 1.
Figure 6:
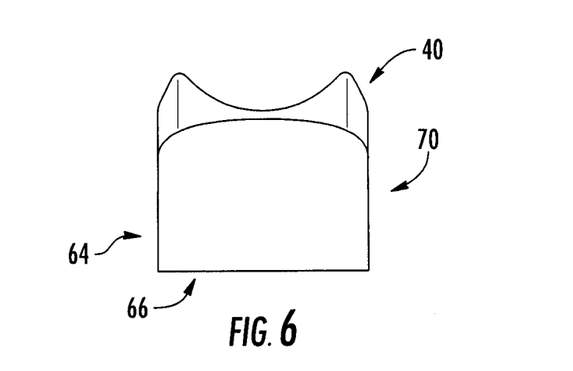
FIG. 6 is a back end view of the arm positioning cushion of FIG. 1.
Figure 7:
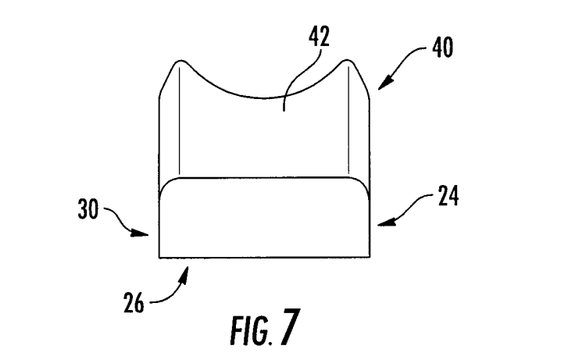
FIG. 7 is a front end view of the arm positioning cushion of FIG. 1.
Figure 8:
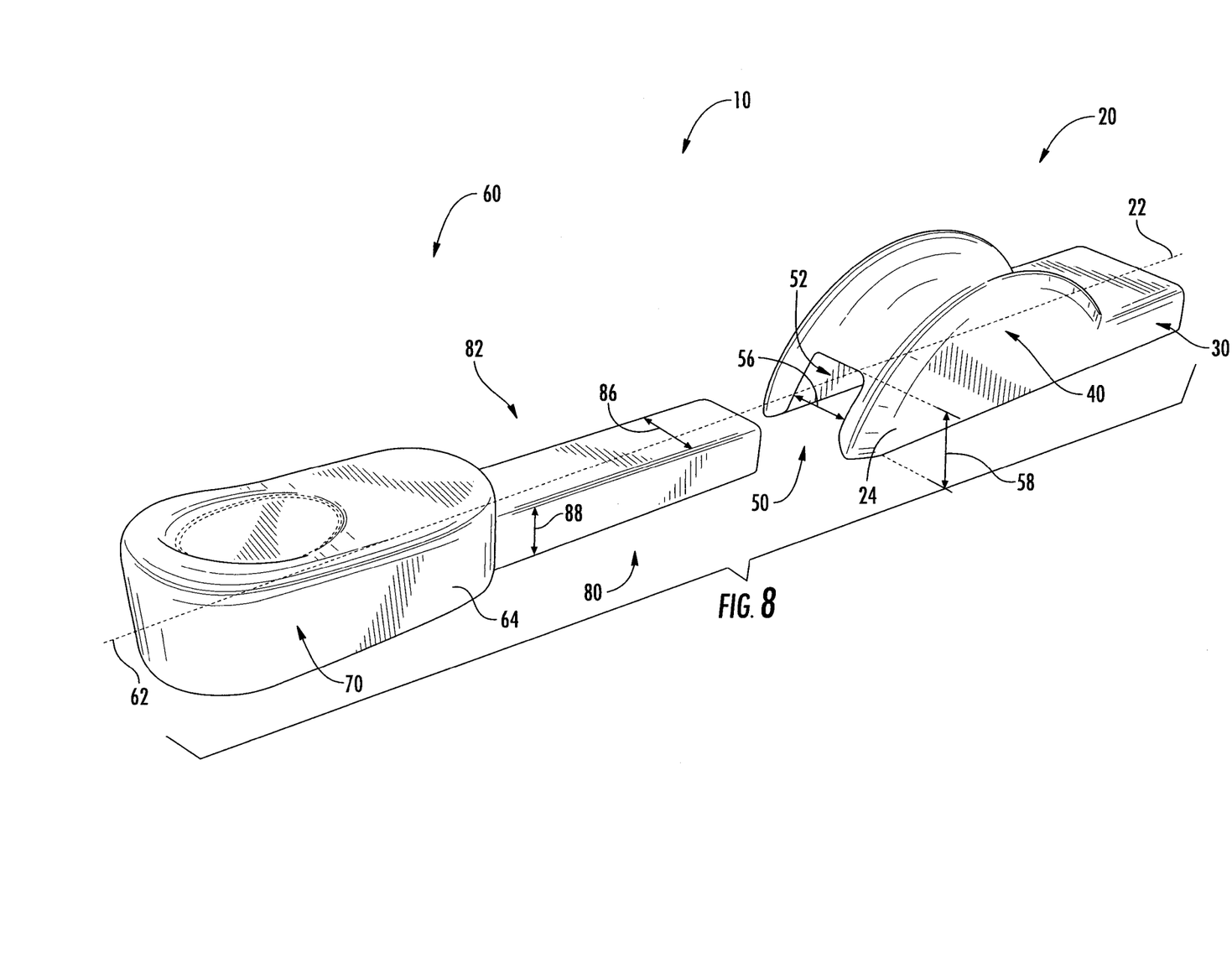
FIG. 8 is a perspective view of the arm positioning cushion of FIG. 1 in an extended/separated configuration.

As shown in FIGS. 4-5 and 8, the forearm support 20 can have a longitudinal axis 22 which passes through the center of the first coupling portion 50, which in this case is an engagement groove or slot 52 formed through the bottom surface 26 and into the base 24 of the forearm support 20. The engagement slot 52 can be formed with a length 54, a width 56, and a depth 58 that adjustably engages with the second coupling portion of the elbow support. In a similar fashion, elbow support 60 can also have a longitudinal axis 62 which passes through the center of the second coupling portion 80, which in this case as a beam or tongue 82 that projects forwardly from the base 64 of the elbow support 60. The tongue 82 can be formed with a length 84, a width 86, and thickness 88 that allows for adjustable engagement with the first coupling portion 50 of the forearm support 20.

In the present embodiment, the tongue 82 of the elbow support 60 and the groove 52 of the forearm support 20 can be configured for sliding engagement with each other to provide the adjustability in the overall length 18 of the arm positioning cushions. However, other methods for adjustably positioning the forearm support 20 and the elbow support 80 relative to each other are possible, and are considered to fall within the scope of the present disclosure. In addition, the association of the slot 52 with the forearm support 20 and the tongue 82 with the elbow support 60 may be arbitrary, and the configuration may be reversed with the tongue extending rearwardly from the forearm support 20 for sliding engagement within a slot formed through the bottom surface 66 and into the base 64 of the elbow support 60.

Figure 10:
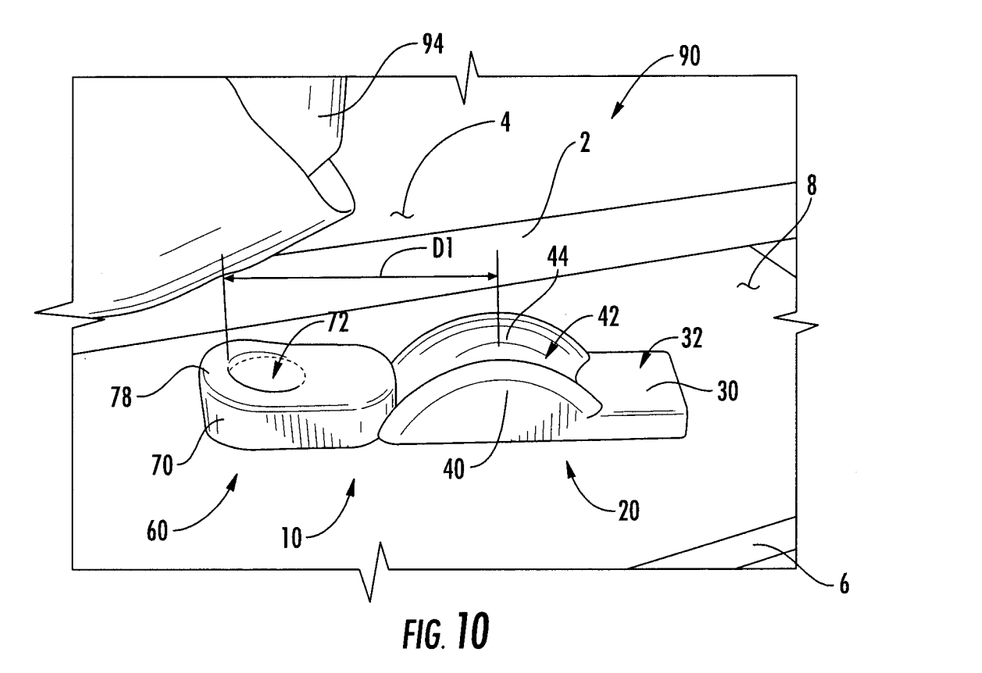
FIG. 10 is a right side view of the arm positioning cushion of FIG. 1 located on a base surface prior to use with patient.
Figure 11:
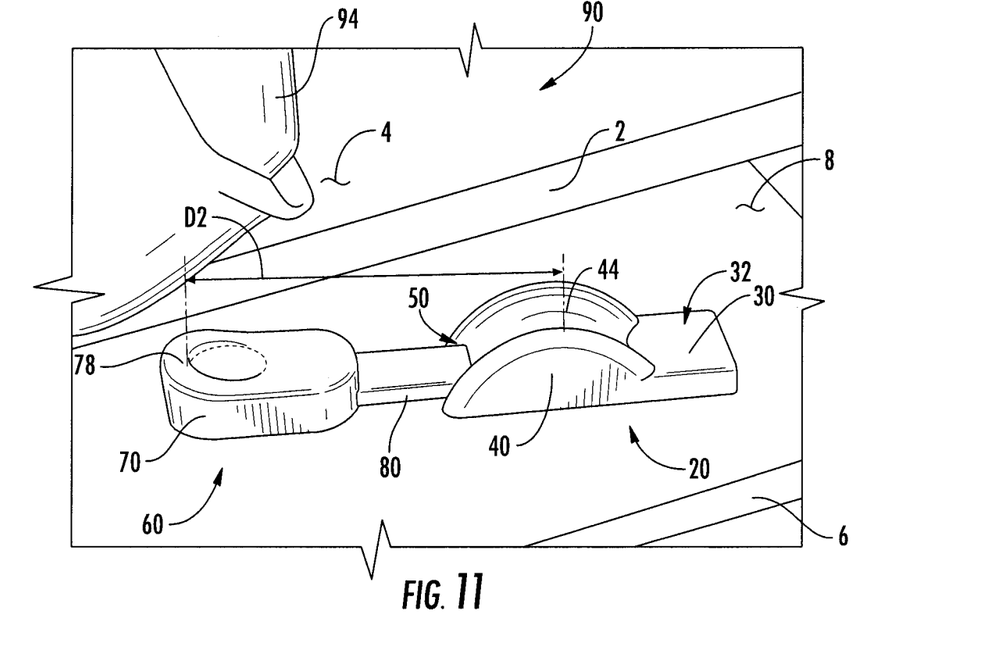
FIG. 11 is another right side view of the arm positioning cushion and patient of FIG. 10.
Figure 12:
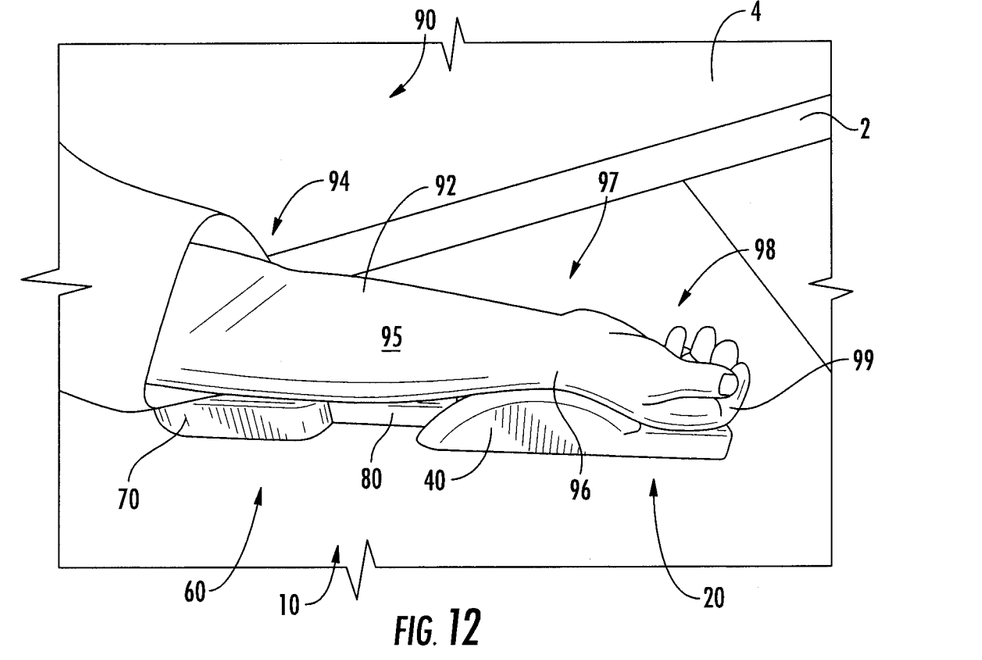
FIG. 12 is yet another right side view of the arm positioning cushion and patient of FIG. 10.
Figure 13:
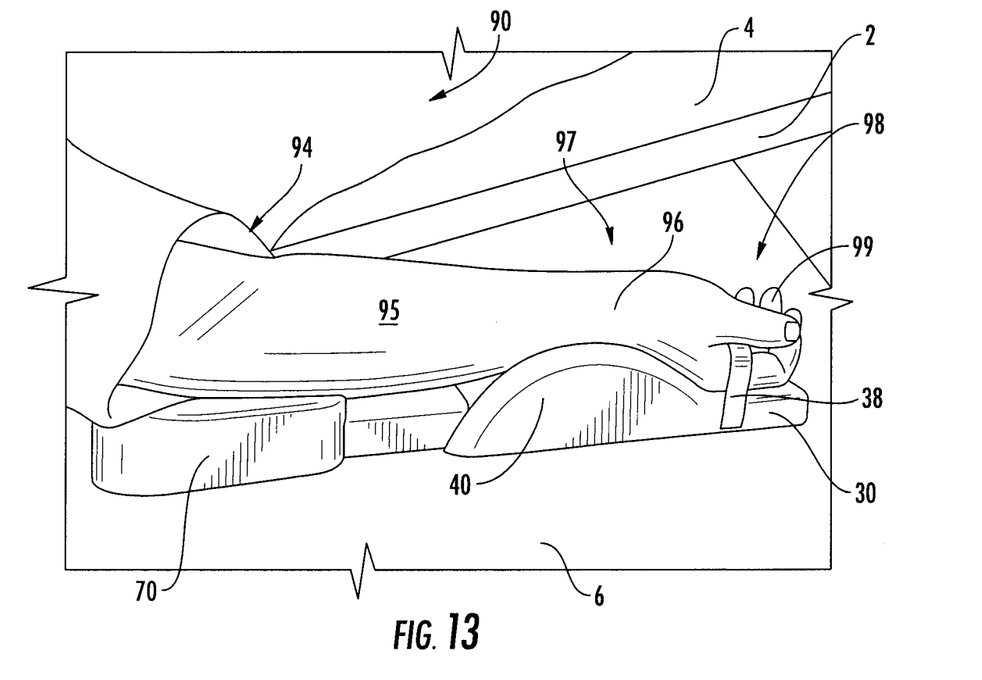
FIG. 13 is yet another right side view of the arm positioning cushion and patient of FIG. 10.

The adjustable engagement between the forearm support 20 and the elbow support 60 allow for the distance between the centerline apex 44 of the wrist support portion 40 and the back ridge 78 of the elbow cradle portion 70 to be varied according to the length of the forearm of the patient. As shown in FIG. 10, for instance, distance D1 between the centerline apex 44 and the back ridge 78, with the tongue 82 of the elbow support 60 being fully engaged within the slot 52 of the forearm support 20 can be about 24 centimeters (or about 9.5 inches). This position can accommodate children and small women. After the elbow support 60 has been pulled rearwardly away from the forearm support, but with the forwardmost portion of the tongue 82 still being engaged within the rearward-most portion of the slot 52, as shown in FIG. 11, the distance D2 between the centerline apex 44 and the back ridge 78 can extend about 35 centimeters (or about 14 inches). This range of positions can accommodate the forearms of most adults, including large males. Thus, the arm positioning cushion 10 of the present disclosure is adjustable to support a wide range of differently-sized forearms.

Figure 9:
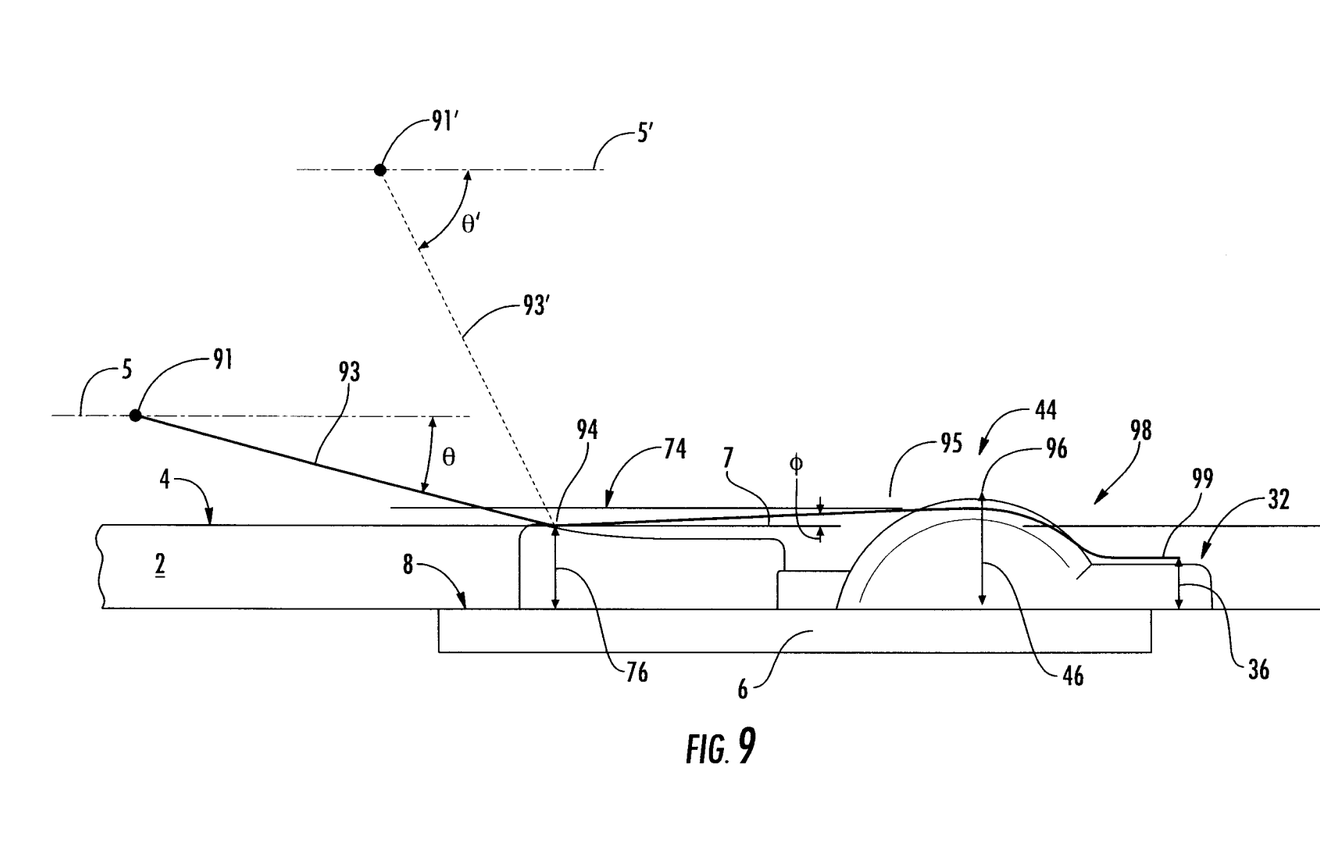
FIG. 9 is a schematic diagram illustration the vertical position of the joints of the arm of the patient using the arm positioning cushion of FIG. 1

Referring now to the schematic drawing of FIG. 9 (in which the arm of the patient is illustrated as a jointed line), the relationships between the height 76 of the elbow contact surface in the depression, the height 46 of the wrist contact surface at the centerline apex, and the height 36 of the fingers contact surface, can be adjusted to provide both comfort to the patient and improved access to the radial artery for the surgeon. As shown on the drawing, for instance, the height 76 of the elbow contact surface can be less than the height 46 of the centerline apex, but greater than the height 36 of the fingers contact surface 32. Thus, the patient's elbow 94 may be elevated above both the base surface 8 and above his fingers 99 resting on the fingers rest portion, and the declination angle θ of the upper arm 93 of the patient from a horizontal reference 5 extending through the shoulder joint 91, is substantially less than it would be if the elbow 94 were resting directly on the base surface 8 of the side support 6. In one aspect, this can improve the comfort of a patient lying on the top surface 4 of the operating table 2 by reducing stress and fatigue at the shoulder joint 91.

Thus, in one aspect of the present disclosure, the height 46 of the centerline apex 44 above the base surface can range from about 6 to about 8 centimeters above the base surface, the height 76 of the depression 74 can range from about 3.5 to about 4.5 centimeters above the base surface 8, and the height 36 of the fingers contact surface 32 can range from about 2.5 to about 3.5 centimeters above the base surface 8.

It is also considered that the arm positioning cushion 10 may be used when the patient is sitting in an upright position, in which case the declination angle θ' of the upper arm 93' of the patient from a horizontal reference 5' extending through the shoulder joint 91 is greater than declination angle θ when the patient is lying down, but still less than it would be if the elbow 94 were resting directly on the base surface 8 of the side support 6. In both configurations, moreover, the inclination angle φ of the forearm 95 of the patient from a horizontal reference 7 extending through the elbow 94 is also less than it would be if the elbow 94 were resting directly on the base surface 8 of the side support 6.

One method of using the arm positioning cushion includes first positioning the forearm support 20 under the hand of the patient so that the back of the patient's wrists falls over the rounded contact surface of the wrist support portion 40. The elbow support 60 can then be grasped and pulled backwards and away from the forearm support 20 until the elbow of the patient may be captured within the elbow cradle portion 70 of the elbow support 60. However, other methods of setting up or configuring the arm positioning cushion 10 in a position that supports the arm of a patient above the base surface and in an orientation that is suitable for vascular radial access procedures are also possible and considered to fall within the scope of the present disclosure.

Although initially directed towards use in radial access vascular procedures, it is contemplated that the arm positioning cushion 10 of the present disclosure may also have application in other medical procedures, including but not limited to brachial cardiac catheterization and other vascular access procedures through either the radial or brachial arteries (near the elbow) or nearby veins.

The foregoing description of the disclosure illustrates and describes various embodiments of the present invention. While the disclosure shows and describes only selected embodiments of the present invention, it will be understood that the present invention further is capable of use in various other combinations and environments. The present invention is also capable of various changes or modifications within the scope of the inventive concept as expressed herein, commensurate with the above teachings, and/or within the skill or knowledge of the relevant art. It will also be understood that certain features and characteristics of each embodiment may be selectively interchanged and applied to other illustrated and non-illustrated embodiments of the disclosure.

What is claimed is:

1. A positioning apparatus for locating and supporting an arm of a patient above a base surface and in an orientation suitable for vascular radial access procedures, the positioning apparatus comprising:
    a forearm support having a first longitudinal axis and including:
        a fingers rest portion having a fingers contact surface located at a first height above the base surface;
        a wrist support portion spaced from the fingers rest portion along the first longitudinal axis and having a wrist contact surface that is upwardly-curved along the first longitudinal axis to define a centerline apex located at a second height above the base surface; and a first coupling portion aligned with the first longitudinal axis; and an elbow support having a second longitudinal axis and including:

an elbow cradle portion comprising an elbow contact surface located at a third height of the base surface; and a second coupling portion aligned with the second longitudinal axis and configured for linearly-adjustable engagement with the first coupling portion to adjustably couple the forearm support to the elbow support, wherein the third height is greater than the first height and less than the second height.

2. The positioning apparatus of claim 1 the forearm support and elbow support comprise a substantially homogeneous cushion material throughout.

3. The positioning apparatus of claim 2, wherein the cushion material further comprises polyethylene foam.

4. The positioning apparatus of claim 2, wherein the cushion material is absorbent or semi-absorbent.

5. The positioning apparatus of claim 1, wherein the wrist contact surface is upwardly curved in a direction transverse to the first longitudinal axis to form upwardly-directed side ridges on both sides of the centerline apex for supporting the sides of the wrist of the patient.

6. The positioning apparatus of claim 1, wherein the elbow contact surface further comprises a back ridge centered on the second longitudinal axis and having a U-shape for cradling the sides of an elbow of a patient.

7. The positioning apparatus of claim 1, wherein the contact surface of the fingers rest portion is substantially planar.

8. The positioning apparatus of claim 1, wherein the wrist contact surface of the wrist support portion is semi-circular.

9. The positioning apparatus of claim 1, wherein the first longitudinal axis and second longitudinal axis are co-linear upon engagement of the second coupling portion With the first coupling portion.

10. A positioning apparatus for locating and supporting an arm of a patient above a base surface and in an orientation suitable for vascular radial access procedures, the positioning apparatus comprising:

a forearm support including a fingers rest portion having a fingers contact surface located at a first height above the base surface, a wrist support portion spaced from the fingers rest portion and having a wrist contact surface that is upwardly-curved to define a centerline apex located at a second height above the base surface, and a first coupling portion; and an elbow support including an elbow cradle portion comprising an elbow contact surface located at a third height of the base surface, and a second coupling portion configured for engagement with the first coupling portion to adjustably couple the forearm support to the elbow support, wherein the third height is greater than the first height and less than the second height.

11. The positioning apparatus of claim 10, wherein the second coupling portion is configured for linearly-adjustable engagement with the first coupling portion.

12. The positioning apparatus of claim 10, wherein the fingers rest portion, the wrist support portion, and the first coupling portion are aligned along a first longitudinal axis and the elbow cradle portion and the second coupling portion are aligned along a second longitudinal axis.

13. The positioning apparatus of claim 12, wherein the first longitudinal axis and second longitudinal axis are co-linear upon engagement of the second coupling portion with the first coupling portion.

14. The positioning apparatus of claim 12, wherein the wrist contact surface is upwardly curved in a direction transverse to the first longitudinal axis to form upwardly-directed side ridges on both sides of the centerline apex for supporting the sides of the wrist of the patient.

15. The positioning apparatus of claim 10, wherein the elbow contact surface further comprises a back ridge centered on the second longitudinal axis and having a U-shape for cradling the sides of an elbow of a patient.

16. The positioning apparatus of claim 10, wherein the forearm support and elbow support comprise a substantially homogeneous cushion material throughout.

17. The positioning apparatus of claim 16, wherein the cushion material further comprises polyethylene foam.

18. The positioning apparatus of claim 16, wherein the cushion material is absorbent or semi-absorbent.

19. A method for locating and supporting an arm of a patient above a base surface and in an orientation suitable for vascular radial access procedures, the method comprising:

positioning a forearm support on a base surface, the forearm support including a fingers rest portion having a fingers contact surface located at a first height above the base surface and a wrist support portion spaced from the fingers rest portion and having a wrist contact surface that is upwardly-curved to define a centerline apex located at a second height above the base surface;

placing a forearm of patient on the forearm support with the back of wrist of the patient contacting the wrist contact surface and the back of the fingers of the patient resting on the fingers contact surface;

positioning an elbow support on the base surface relative to the forearm support, the elbow support being adjustably coupled to the forearm support and including an elbow cradle portion comprising an elbow contact surface located at a third height of the base surface; and placing the elbow of the patient in the elbow cradle portion so that the height of the elbow of the patient above the base surface is greater than the height of the fingers of the patient above the base surface but less than the height of the wrist of the patient above the base surface.

20. The method of claim 19, wherein positioning the elbow support on the base surface further comprises linearly withdrawing the elbow support that is in linearly-adjustable engagement with the forearm support in a direction away from the forearm support.

* * * * *

UNITED STATES PATENT AND TRADEMARK OFFICE
CERTIFICATE OF CORRECTION

PATENT NO.      : 9,125,784 B2
APPLICATION NO. : 13/940541
DATED           : September 8, 2015
INVENTOR(S)     : Larry Van Thomas Crisco et al.

It is certified that error appears in the above-identified patent and that said Letters Patent is hereby corrected as shown below:

In The Claims

Column 7, Line 12-13 reads, ". . . portion to adjust ably couple the . . ." which should read ". . . portion to adjustably couple the . . ."

Column 7, Line 16 reads, ". . . apparatus of claim 1 the forearm . . ." which should read ". . . apparatus of claim 1 wherein the forearm . . ."

Column 7, Line 38 reads, ". . . second coupling portion With the . . ." which should read ". . . second coupling portion with the . . ."

Signed and Sealed this
Twenty-ninth Day of March, 2016

Michelle K. Lee
*Director of the United States Patent and Trademark Office*